(12) United States Patent
Hsu

(10) Patent No.: US 8,920,854 B2
(45) Date of Patent: Dec. 30, 2014

(54) ORAL CARE COMPOSITIONS FOR TREATING XEROSTOMIA

(75) Inventor: Stephen D. Hsu, Evans, GA (US)

(73) Assignee: Georgia Regents Research Institute, Augusta, GA (US)

(*) Notice: Subject to any disclaimer, the term of this patent is extended or adjusted under 35 U.S.C. 154(b) by 96 days.

(21) Appl. No.: 12/739,340

(22) PCT Filed: Feb. 22, 2010

(86) PCT No.: PCT/US2010/024906
§ 371 (c)(1),
(2), (4) Date: Oct. 25, 2010

(87) PCT Pub. No.: WO2010/099062
PCT Pub. Date: Sep. 2, 2010

(65) Prior Publication Data
US 2011/0300241 A1    Dec. 8, 2011

Related U.S. Application Data

(60) Provisional application No. 61/208,453, filed on Feb. 25, 2009.

(51) Int. Cl.
*A61K 36/82* (2006.01)
*A61K 36/00* (2006.01)
*A01N 43/16* (2006.01)
*A61K 31/35* (2006.01)

(52) U.S. Cl.
CPC .............. *A01N 43/16* (2013.01); *A61K 31/35* (2013.01)
USPC .......................................... 424/729; 424/725

(58) Field of Classification Search
None
See application file for complete search history.

(56) References Cited

U.S. PATENT DOCUMENTS

| 6,159,459 | A | * | 12/2000 | Hunter et al. ............... 424/78.08 |
| 2005/0090864 | A1 | * | 4/2005 | Pines et al. ....................... 607/2 |
| 2006/0204599 | A1 | | 9/2006 | Wheat | |
| 2007/0048224 | A1 | * | 3/2007 | Howell et al. .................. 424/9.1 |
| 2009/0047408 | A1 | * | 2/2009 | Unno et al. ..................... 426/597 |
| 2009/0117146 | A1 | * | 5/2009 | Khan et al. ............... 424/195.17 |

FOREIGN PATENT DOCUMENTS

WO    WO2006135785 A2 * 12/2006

OTHER PUBLICATIONS

Baudouin, at al., "Current treatments of xerophthalmia in Sjögren's syndrome", Rev Med Interne, 25:376-82 (2004).
Cassolato and Turnbull, "Xerostomia: clinical aspects and treatment", Gerodontology, 20:64-77 (2003).
Fox, "Sjögren's syndrome. Controversies and progress", Clin Lab Med., 17 (3):431-44 (1997).
Fox, "Sjogren's syndrome: evolving therapies", Exp Opin Investig Drugs, 12:247-54 (2003).
Gillespie, et al., "Effects of oral consumption of the green tea polyphenol EGCG in a murine model for human Sjogren\s syndrome, an autoimmune disease", Life Sci., 83:581-88 (2008).
Hsu and Dickinson, "Green Tea: A New Approach to Managing Oral manifestations of Sjogren\s Syndrome and Skin Manifestations of Lupus", J Biochem. Mol. Bio, 39:229-39 (2006).
Hsu, et al., "Green tea polyphenols reduce autoimmune symptoms in a murine model for human Sjogren's syndrome and protect human salivary acinar cells from TNF-alpha-induced cytotoxicity", Autoimmunity, 40(2):138-47 (2007).
Hsu, et al., "Inhibition of autoantigen expression by (−)-Epigallocatechin-3-gallate (the major constituent of green tea) in normal human cells", J Pharma. and Exper. Therap., 315:805-11 (2005).
Porter at al., "An update of the etiology and management of xerostomia", Oral Surg Oral Med Oral Pathol Oral Radiol Endod., 97:28-46 (2004).
Sreebny and Valdini, "Xerostomia. A neglected symptom",Arch Intern Med., 147:1333-7 (1987).

* cited by examiner

*Primary Examiner* — Chris R Tate
*Assistant Examiner* — Randall Winston
(74) *Attorney, Agent, or Firm* — Pabst Patent Group LLP

(57) ABSTRACT

Disclosed herein are oral care compositions for promoting salivary flow. Thus, also disclosed are methods of treating and preventing xerostomia. The oral care compositions can contain all-natural ingredients, including, for example, green tea polyphenols and *jaborandi* extract.

29 Claims, 14 Drawing Sheets

ORAL CARE COMPOSITIONS FOR TREATING XEROSTOMIA

CROSS-REFERENCE TO RELATED APPLICATIONS

This application claims benefit of U.S. Provisional Application No. 61/208,453, filed Feb. 25, 2009, which is hereby incorporated herein by reference in its entirety.

STATEMENT REGARDING FEDERALLY SPONSORED RESEARCH

This invention was made with government support under Grant CA097458-01A awarded by the National Institutes of Health. The government has certain rights in the invention.

BACKGROUND

Xerostomia (the perception of dry mouth) affects up to 40% of U.S. adults (Cassolato S F, et al. 2003). It has several causes, including chronic medication, diabetes, and Sjogren's syndrome (SS), and can have a major negative impact on the quality of life (Sreebny L M, et al. 1987). Artificial lubricants are commonly used as saliva substitutes, and dentrifices have been devised that provide some of the salivary protective functions (Baudouin C, et al. 2004). In recent years, prescription orally ingested salivary stimulants, such as cevimeline (EVOXAX), have been approved by the FDA for xerostomia (Cassolato S F, et al. 2003; Fox R I 2003; Porter S R, et al. 2004). However, they are associated with significant side effects. Thus, new and improved approaches to prevention and therapy of xerostomia are in urgent need.

BRIEF SUMMARY

In accordance with the purpose of this invention, as embodied and broadly described herein, this invention relates to oral care compositions for promoting salivary flow and methods of treating and preventing xerostomia. The oral care compositions can contain all-natural ingredients, including, for example, green tea polyphenols and *jaborandi* extract.

Additional advantages of the disclosed composition(s) and method(s) will be set forth in part in the description which follows, and in part will be understood from the description, or may be learned by practice of the disclosed composition(s) and method(s). The advantages of the disclosed composition(s) and method(s) will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed methods and compositions.

FIG. 7A shows PCNA immunostaining. Solid arrows point to representative nuclear staining of ductal cells; open arrows to areas of cytoplasmic staining; gray arrows to PCNA immunostaining in the lumen of some ducts. FIG. 7B shows Ki-67 immunostaining. Solid arrows point to representative nuclear staining of ductal cells.

FIGS. 8C and 8F show statistical analysis of peroxiredoxin 6 and Catalase-positive cells. Black arrows point to ductal cells; open arrow to acinar cells (FIG. 8B).

DETAILED DESCRIPTION

Figure 1A:
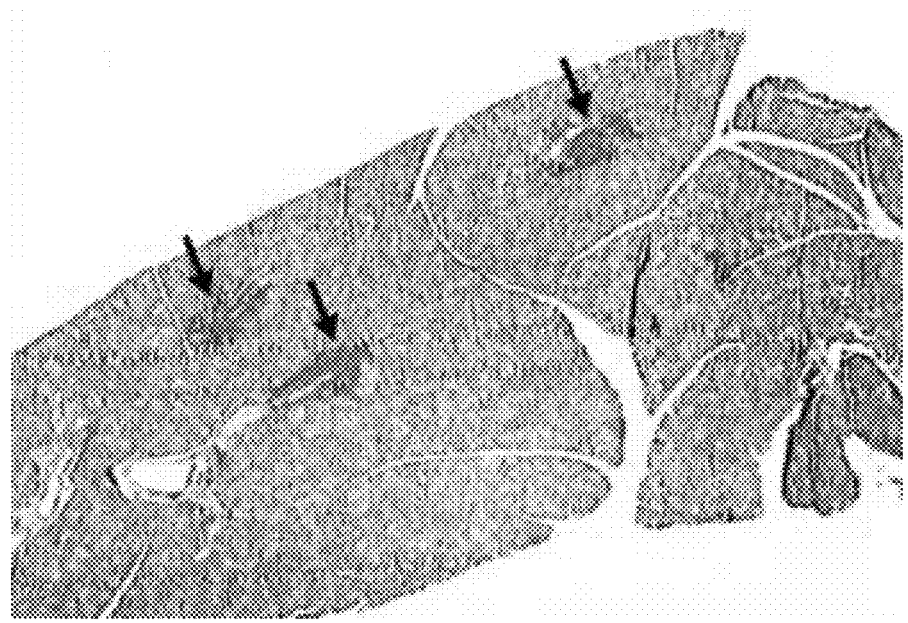
FIGS. 1A-1B show representative H&E stained submandibular gland sections from water-fed (FIG. 1A) and GTPs/water-fed (FIG. 1B) NOD mice. Arrows point to local lymphocyte infiltrations comprising 50 or more lymphocytes.

The disclosed methods and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed composition(s) and method(s). These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. Thus, if a class of molecules A, B, and C is disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F is specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the composition(s) and method(s) described herein. Such equivalents are intended to be encompassed by the appended claims.

It is understood that the disclosed composition(s) and method(s) are not limited to the particular methodology, protocols, and reagents described as these may vary. It is also to be understood that the terminology used herein is for the purpose of describing particular embodiments only and is not intended to limit the scope of the present invention which will be limited only by the appended claims.

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural referents unless the context clearly dictates otherwise. Thus, for example, reference to "a extract" includes a plurality of such extracts, reference to "the extract" is a reference to one or more extracts and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that the throughout the application, data are provided in a number of different formats, and that these data represent endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

The term "substantially" with respect to the stereochemistry at carbon a refers to greater than 95%, greater than 97%, greater than 98%, greater than 99%, greater than 99.5%, or 100% of one enantiomer with respect to the other enantiomer. The terms "R" and "S" with respect to the stereochemistry at carbon a is also referred to in the art as "D" and "L," respectively. The term "substantially" as defined above also applies to diastereoisomers, where a compound can be a substantially pure diastereoisomer.

Variables such as $R^1$, $R^2$, $R^3$, and n used throughout the application are the same variables as previously defined unless stated to the contrary.

Throughout the description and claims of this specification, the word "comprise" and variations of the word, such as "comprising" and "comprises," means "including but not limited to" and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Provided herein is an oral care composition, comprising at least one green tea polyphenol (GTP), or the pharmaceutically acceptable salt or ester thereof. Polyphenols are a group of chemical substances found in plants, characterized by the presence of more than one phenol unit or building block per molecule. Polyphenols are generally divided into hydrolyzable tannins (gallic acid esters of glucose and other sugars) and phenylpropanoids, such as lignins, flavonoids, and condensed tannins. The largest and best studied polyphenols are the flavonoids, which include several thousand compounds, among them the flavonols, flavones, catechins, flavanones, anthocyanidins, and isoflavonoids.

Catechins are abundant in teas derived from the tea-plant *Camellia sinensis*. White tea, green tea, oolong, pu-erh tea and black tea are all harvested from this species, but are processed differently to attain different levels of oxidation.

Catechin and epicatechin are epimers, with (−)-epicatechin and (+)-catechin being the most common optical isomers found in nature. Catechin gallates are gallic acid esters of the catechins; such as epigallocatechin gallate (EGCG), which is commonly the most abundant catechin in tea.

In some aspects, the GTP of the disclosed oral composition has the following chemical structure or the pharmaceutically acceptable salt or ester thereof:

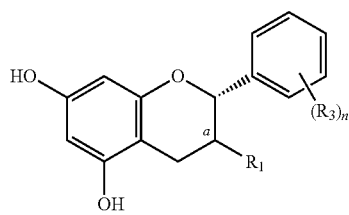

wherein $R_1$ is H, OH or gallic acid (GA);
$R_3$ is OH;
n is from 1 to 5; and
the stereochemistry at carbon a is substantially R or S.

Thus, in some aspects, the GTP of the disclosed oral composition has the following chemical structure or the pharmaceutically acceptable salt or ester thereof:

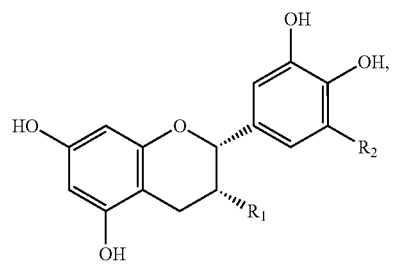

wherein $R_1$ is H, OH or gallic acid (GA), and
wherein $R_2$ is OH or H.

The gallic acid (GA) of the disclosed oral composition can have the following chemical structure or the pharmaceutically acceptable salt or ester thereof:

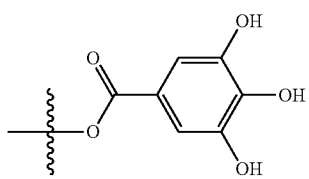 [SMILES: *OC(=O)c1cc(O)c(O)c(O)c1]

Thus, in some aspects, the GTP of the disclosed oral composition is epigallocatechin-3-gallate (EGCG) or the pharmaceutically acceptable salt or ester thereof. Thus, in some aspects, the GTP of the disclosed oral composition has the following chemical structure or the pharmaceutically acceptable salt or ester thereof:

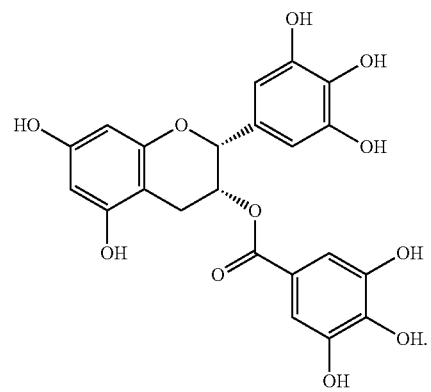 [SMILES: O=C(O[C@@H]1Cc2c(O)cc(O)cc2O[C@@H]1c1cc(O)c(O)c(O)c1)c1cc(O)c(O)c(O)c1]

Thus, in some aspects, the GTP of the disclosed oral composition is epigallocatechin (EGC) or the pharmaceutically acceptable salt or ester thereof. Thus, in some aspects, the GTP of the disclosed oral composition has the following chemical structure or the pharmaceutically acceptable salt or ester thereof:

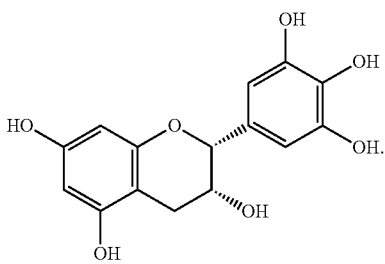 [SMILES: Oc1cc(O)c2c(c1)O[C@H](c1cc(O)c(O)c(O)c1)[C@H](O)C2]

Thus, in some aspects, the GTP of the disclosed oral composition is epicatechin gallate (ECG) or the pharmaceutically acceptable salt or ester thereof. Thus, in some aspects, the GTP of the disclosed oral composition has the following chemical structure or the pharmaceutically acceptable salt or ester thereof:

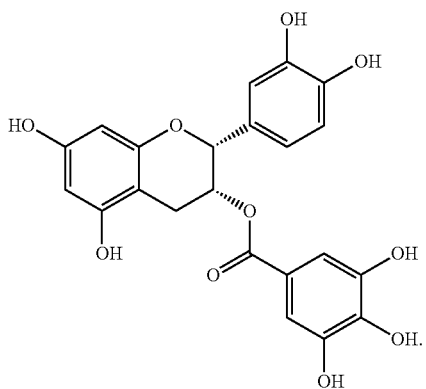 [SMILES: O=C(O[C@@H]1Cc2c(O)cc(O)cc2O[C@@H]1c1ccc(O)c(O)c1)c1cc(O)c(O)c(O)c1]

Thus, in some aspects, the GTP of the disclosed oral composition is epicatechin (EC) or the pharmaceutically acceptable salt or ester thereof. Thus, in some aspects, the GTP of the disclosed oral composition has the following chemical structure or the pharmaceutically acceptable salt or ester thereof:

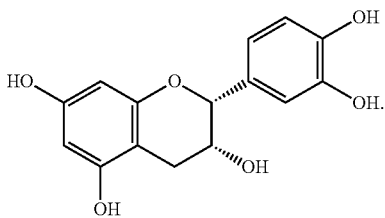 [SMILES: Oc1cc(O)c2c(c1)O[C@H](c1ccc(O)c(O)c1)[C@H](O)C2]

Also disclosed herein are all epimers and optical isomers of there herein disclosed GTP structures. For example, catechin and epicatechin are epimers, with (−)-epicatechin and (+)-catechin being the most common optical isomers found in nature.

Thus, in some aspects, the GTP of the disclosed oral composition is catechin (+C) or the pharmaceutically acceptable salt or ester thereof. Thus, in some aspects, the GTP of the disclosed oral composition has the following chemical structure or the pharmaceutically acceptable salt or ester thereof:

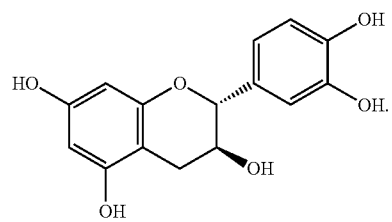 [SMILES: Oc1cc(O)c2c(c1)O[C@H](c1ccc(O)c(O)c1)[C@@H](O)C2]

The GTP of the disclosed oral composition can be in a green tea leaf extract or green tea powder. Such natural sources of the disclosed GTPs are known in the art and commercially available.

Any of the GTPs useful herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group, can be prepared by reaction of the carboxylic acid-containing compound with ammonia or a substituted amine.

In some aspects the GTP is a fatty acid ester derivative. For example, Mori S, et al. (Bioorg Med Chem. Lett. 2008 Jul. 15; 18(14):4249-52) is disclosed herein by reference for its teaching of EGCG monoester derivatives. Briefly, fatty acids can be introduced to the phenolic hydroxyl groups of the GTPs disclosed herein. These fatty acid derivatives can, for example, be prepared by lipase-catalyzed transesterification. In some aspects, the fatty acid ester is a monoester. In some aspects, the GTP monoesters are modified with saturated acyl groups having, for example, 4-20 carbon atoms. Thus, the GTP monoesters can be modified with butanoyl (C4), pentanoyl (C5), hexanoyl (C6), heptanoyl (C7), octanoyl (C8), decanoyl (C10), lauroyl (C12), palmitoyl (C16), or eicosanoyl (C20) groups. Thus, the GTP monoester can be EGCG-monopalmitate.

The oral care composition provided herein can further comprise at least one salivary gland activating agent. Examples of salivary gland activating components include parasympathomimetic agents, cholinesterase inhibitors, and calcium ion releasing agents. For example, the salivary gland activating agent can be pilocarpine, muscarine, acetylcholine, ryanodine, or caffeine. The salivary gland activating agent can be an extract of a plant such as *Cola acuminata, Cola*

*nitida, jaborandi*, white birch, honeysuckle, American ginseng, *houttuynia cordata*, garlic, hibiscus, hop, *Actinidia polygama*, linden or rose hip.

Pilocarpine is a parasympathomimetic alkaloid obtained from the leaves of tropical American shrubs from the genus *Pilocarpus*. *Pilocarpus* is a genus of about 13 species of plants belonging to the family Rutaceae, native to the neotropics of South America. Various species are important pharmacologically. Many of the species have the common name *Jaborandi*.

Pilocarpine is a non-selective muscarinic receptor agonist in the parasympathetic nervous system, which acts therapeutically at the muscarinic acetylcholine receptor M3 due to its topical application. Pilocarpine is available under several trade names such as: Diocarpine (Dioptic), Isopto Carpine (Alcon), Miocarpine (CIBA Vision), Ocusert Pilo-20 and -40 (Alza), Pilopine HS (Alcon), Salagen (MGI Pharma), Scheinpharm Pilocarpine (Schein Pharmaceutical), and Timpilo (Merck Frosst).

To prepare pilocarpine, the powdered leaf of a *Pilocarpus* can be subjected to extracted forotoal alkaloid with ethanol, acidified with HCL with solvents removed under reduced pressure, and resultant aqueous residue neutralized with ammonia and kept aside till all the resin is settled down completely. It can be filtered and concentrated by sugar solution to a small volume made alkaloid with ammonia and finally extracted with chloroform. The solvent can then removed under reduced pressure.

Alternatively, the salivary gland activating agent can be an extract of a *Pilocarpus* such as Jaborandi. Jaborandi contains three alkaloids, pilocarpine, isopilocarpine, and pilocarpidine. Thus, the salivary gland activating agent can comprise pilocarpine, isopilocarpine, and pilocarpidine. However, isopilocarpine can be converted into pilocarpine by heating with alcoholic solution of potassium hydroxide. Thus, the salivary gland activating agent can be dried leaflets of *Pilocarpus Jaborandi*. Other such natural sources of pilocarpine are known in the art and commercially available.

Thus, in some aspects, the disclosed oral care composition comprises epigallocatechin-3-gallate (EGCG), or the pharmaceutically acceptable salt or ester thereof, and pilocarpine. Thus, in some aspects, the disclosed oral care composition comprises epigallocatechin-3-gallate (EGCG), or the pharmaceutically acceptable salt or ester thereof, and *Jaborandi* extract.

The herein disclosed oral care composition can further comprise at least one taste stimulating component. Examples of the taste stimulating component include organic acids and flavoring substances. Examples of the organic acids include citric acid, isocitric acid, malic acid, acetic acid, oxalic acid, malonic acid, succinic acid, glutaric acid, maleic acid, fumaric acid, aconitic acid, lactic acid, tartaric acid, pyruvic acid, ascorbic acid, aldonic acid, and uronic acid. In addition, plum vinegar, apple vinegar, and chips, powder or extract of citrus such as lemon, orange, citron, or Chinese citron can be given as examples. Examples of the flavoring substance include amino acids (salts), nucleic acids, dipeptides, tripeptides, and oligopeptides, more specifically, sodium glutamate, inosinic acid and guanylic acid. Thus, in some aspects, the disclosed oral care composition comprises citric acid.

Thus, in some aspects, the disclosed oral care composition comprises epigallocatechin-3-gallate (EGCG), or the pharmaceutically acceptable salt or ester thereof, pilocarpine, and citric acid. Thus, in some aspects, the disclosed oral care composition comprises epigallocatechin-3-gallate (EGCG), or the pharmaceutically acceptable salt or ester thereof, *Jaborandi* extract, and citric acid.

The oral care composition disclosed herein can further comprise sweeteners such as sorbitol, saccharin sodium, acesulfame potassium, aspartame, glycyrrhizin, perillartine, thaumatin, aspartylphenylalanyl methyl ester and xylitol. The content thereof can, for example, be in an amount of about 2, 3, 4, 5, 6, 7, 8, 9, 10, 11, 12, 13, 14, 15, 16, 17, 18, 19, 20, 25, 30, 35, 40, 45, 50, 60, 70, 80, 90, 95 percent by weight of the total composition. Thus, the content thereof can, for example, be in an amount of about 1% to about 90%, about 3% to about 20% by weight, or about 4% to about 15% by weight, or any other range values in between, based on the total composition.

Thus, in some aspects, the disclosed oral care composition comprises epigallocatechin-3-gallate (EGCG), or the pharmaceutically acceptable salt or ester thereof, pilocarpine, citric acid, and xylitol. Thus, in some aspects, the disclosed oral care composition comprises epigallocatechin-3-gallate (EGCG), or the pharmaceutically acceptable salt or ester thereof, *Jaborandi* extract, citric acid, and xylitol.

In some aspects, the oral care composition disclosed herein is a dentifrice preparation. As used herein, term "dentifrice" or "dentifrices" refer to products which remain in the mouth for a relatively short period of time, in which they are intimately contacted with substantially all surfaces of the teeth, and are then removed. Non-limiting examples of such products include toothpastes, prophylactic pastes, tooth polishes, jelly, gels, professional gels and other related professional products, as well as mouth washes, sprays, mouth rinses, dental flosses, mouth rings, thin strips, chewing gums, lozenges, mints, tablets, edible food products, and the like.

The oral composition can further comprise one or more lubricants. Non-limiting examples of suitable lubricants include magnesium stearate, stearic acid, palmitic acid, calcium stearate, talc, polyethylene glycol, colloidal silicon dioxide, sodium stearyl fumarate, carnauba wax and the like and mixtures thereof.

In some aspects, the oral care composition disclosed herein further comprises an orally acceptable carrier or excipient. Thus, disclosed herein is an oral care composition for alleviating or preventing xerostomia, comprising one or more green tea polyphenols (GTP), *Jaborandi* extract, citric acid, xylitol, and an orally acceptable carrier or excipient. Thus, disclosed herein is an oral care composition for alleviating or preventing xerostomia, comprising epigallocatechin-3-gallate (EGCG), *Jaborandi* extract, citric acid, xylitol, and an orally acceptable carrier or excipient.

The oral care composition disclosed herein can in some aspects comprise 10 mg/unit to 100 mg/unit of the one or more GTPs. The oral care composition disclosed herein can in some aspects comprise 5 mg/unit to 50 mg/unit of *Jaborandi* extract.

The oral care composition disclosed herein can further comprise flavor components. These flavor components can serve not only to give a palatable flavor to the oral care composition, but can act as natural antibacterial agents and preservatives at the same time. The oils suitable for use in the present invention include, but are not limited to, citric oil, lemon oil, lime oil, lemongrass oil, orange oil, sweet orange oil, grapefruit oil, pomegranate oil, apricot oil extract, tangerine extract, tangelo oil, peppermint oil, spearmint oil, sage oil, rosemary oil, cinnamon oil, winter green oil, clove oil, eucalyptus oil, ginger oil, sassafras oil, menthol, arvensis mint oil, synthetic mint flavors and oils, carvone, eugenol, methyleugenol, methyl salicylate, methyl eugenol, thymol, anethole, millefolium extract, chamomile, lavender oil, myrrh, eugenol, tea tree oil, sage oil, mallow, limonene, ocimene, n-decyl alcohol, citronellol, alpha-terpineol, linalol, ethyllinalol, thyme, almond oil, nutmeg, and vanillin. Either one of these flavors or a mixture of two or more of these flavors can be used in the dentifrice composition.

The oral care composition disclosed herein can further comprise one or more surfactants or a mixture of compatible surfactants. Suitable surfactants are those which are reasonably stable throughout a wide pH range, for example, anionic, cationic, nonionic or zwitterionic surfactants. In an illustrative embodiment, the surfactant is a non-ionic surfactant useful as a foaming agent. Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. The surfactant or mixtures of compatible surfactants can, for example, be present in the compositions of the present invention in an amount of about 0.1% to about 5.0%, about 0.3% to about 3.0%, and about 0.5% to about 2.0% by weight of the total composition.

The oral care composition disclosed herein can further comprise one or more abrasives. Suitable abrasives include, but are not limited to, silica abrasives such as precipitated silicas having a mean particle size of up to about 20 microns, such as Zeodent 115® marketed by J. M. Huber. The abrasive material can be one that is compatible with the composition of interest and does not excessively abrade dentin. Suitable abrasives include for example silicas including gels and precipitates, insoluble polymetaphosphate, hydrated alumina, resinous abrasives such as polymerized resins (e.g., ureas, melamines, cross-linked epoxides, phenolics, and the like), and mixtures thereof.

The oral care composition disclosed herein can further comprise about 0% to about 40% by weight water. Water used in the preparation of an oral care composition can be deionized and free of organic impurities.

In addition to the above-described components, the oral care composition disclosed herein can further comprise a variety of optional ingredients and vehicles generally used for preparations for use in the oral cavity, such as dentifrices. These optional components include, but are not limited to, such components as abrasives, surfactants, thickening agents, buffers, humectants, preservatives, antibiotic, anti-caries agents, anticalculus (anti-tartar) agents, nutrients, and vitamins.

Provided in Table 1 below is an example of a natural formula for the oral care composition disclosed herein.

TABLE 1

Exemplary Formula

| Ingredients | % w/v |
|---|---|
| Lozenge/Pastille base | 56 |
| Glycerin or olive oil (optional) | 5 |
| Green tea extract | 10 (100 mg) |
| Jaborandi extract | 2 (20 mg) |
| Xylitol | 10 (100 mg) |
| Citric acid | 5 (50 mg) |
| Gelatin | |
| De-bitter agent | 2 |
| Carboxymethyl cellulose | 10 |
| Zinc | 0.1 |
| Total | 100 |

Also disclosed herein is a method of treating or preventing xerostomia, comprising administering to a subject in need thereof an effective amount of an oral care composition disclosed herein. The disclosed oral composition can be administered to the subject in any manner that puts the oral care composition in contact with the salivary glands of the subject for at least 1, 2, 3, 4, 5, 6, 7, 8, 9, or 10 minutes. Suitable delivery vehicles are known and disclosed herein for this purpose.

In some aspects, oral consumption of the GTPs, such as drinking green tea, does not result in sufficient exposure of the GTPs to the salivary glands. Moreover, in some aspects, oral consumption of enough GTP to have the desired effect would cause side-effects due to systemic exposure. Thus, in some aspects, the GTP is administered in a manner other than consumption, such as consumption in a tea. In contrast, administration of the GTP using a dentifrice composition can provide local release of the agents to the salivary gland.

In some aspects of the method, the subject has been diagnosed with an autoimmune disease. For example, in some aspects, the subject has been diagnosed with Sjögren's syndrome. In some aspects, the subject has recently undergone radiation or chemotherapy. In some aspects, the subject has been diagnosed with diabetes.

Also disclosed herein is a use for green tea polyphenol (GTP) for the preparation of an oral care composition disclosed herein for alleviating or preventing xerostomia.

The exact amount of the compositions required can vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage can vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

The materials described above as well as other materials can be packaged together in any suitable combination as a kit useful for performing, or aiding in the performance of, the disclosed method. It is useful if the kit components in a given kit are designed and adapted for use together in the disclosed method.

Disclosed herein are oral care compositions comprising two or more ingredients. Thus, also disclosed is a kit comprising two or more oral compositions separately comprising the herein disclosed ingredients. These two or more oral compositions can be taken (administered) simultaneously to combine the two or more ingredients in the mouth.

For example, disclosed are kits for promoting salivary flow, the kit comprising a first oral care composition comprising a GTP, such as EGCG) and a second oral care composition comprising a salivary gland activating agent, such as *jaborandi* extract. The first or second oral care composition can further comprise a taste stimulating component, such as citric acid. The first or second oral care composition can further comprise a sweetener such as xylitol. Other such combinations for preparation of a kit can be envisioned based on the ingredients disclosed herein.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

An animal study was conducted to examine whether a green tea extract (GTPs) fed prior to development of exocrinopathy is protective against SS-like symptoms and salivary gland lymphocyte infiltration.

Lymphocyte Infiltration.

Figure 1B:
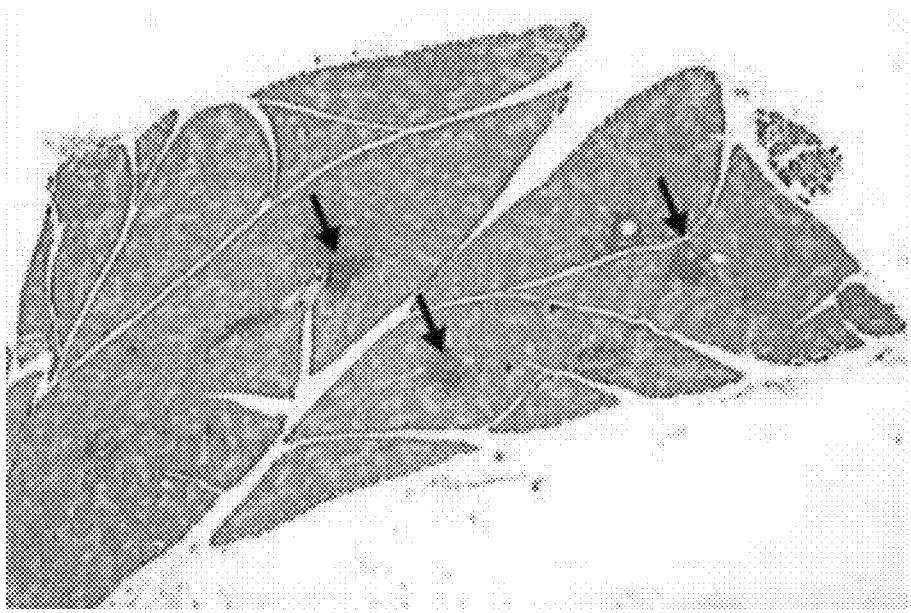
Figure 2:
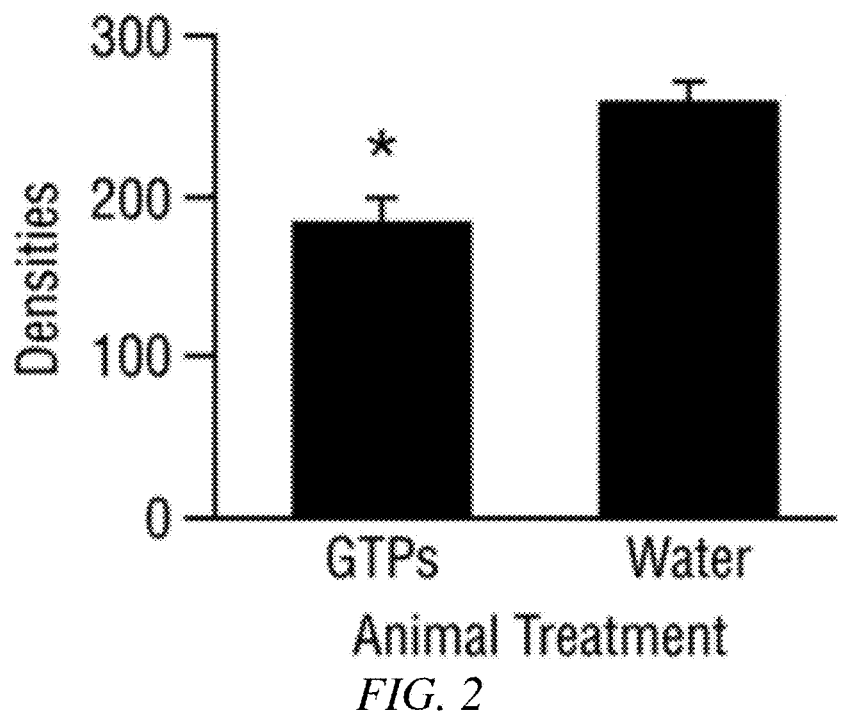
FIG. 2 shows average focal area of submandibular lymphocyte infiltration in NOD mice either fed with GTPs/water or water only. Relative density units were generated by BIOQUANT NOVA PRIME 6.75 software, representing area sizes. Areas are proportional to cell number. Error bars are standard error of means (SEM). Result was analyzed by two-tailed t-test analysis (p=0.006). n=83 foci/group.

Quantitative analysis of animals 3 weeks after the onset of diabetes (>20 weeks of age) showed a significant difference between the animal treatment groups in the number of inflammatory cells/infiltrate, with fewer cells in the salivary glands of GTPs/water-fed vs. water only animals (p=0.006, two-tailed t-test, n=83 foci/group) (FIGS. 1 and 2). That is, GTPs possess an anti-inflammatory effect in an SS model in vivo.

Serum Total Autoantibodies.

Figure 3:
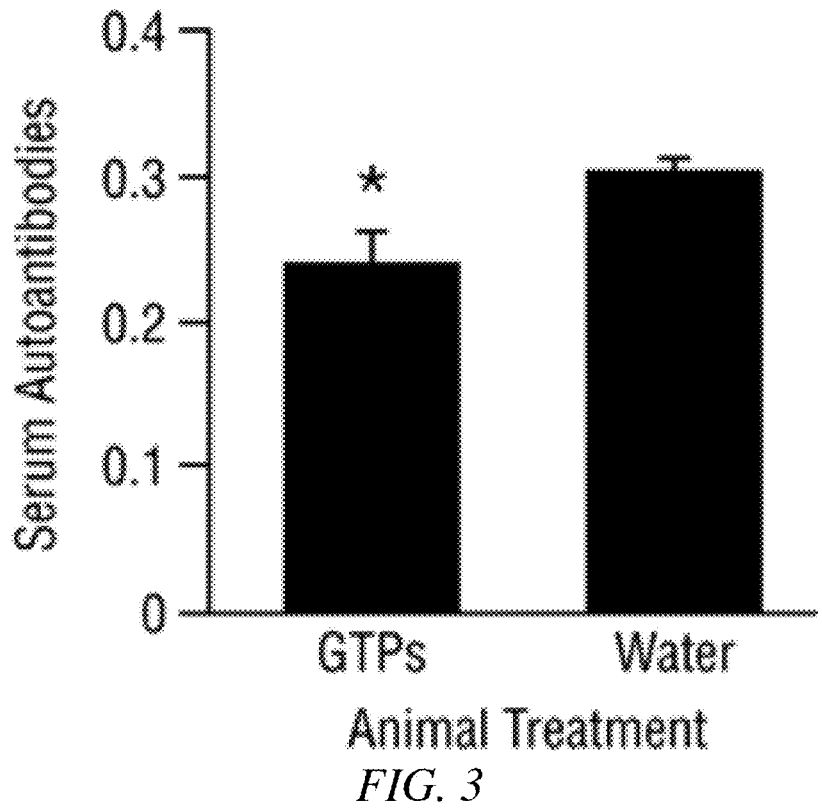
FIG. 3 shows serum autoantibody concentrations in NOD mice after 3 week-progression of disease in each mouse. Values of each bar represent optic absorption measurements. y-error bars represent SEM. Two-tailed student t-test analysis, P=0.036, n=27.

Serum samples from the two groups were examined by ELISA assays for anti-SS-associated autoantibodies using the Mouse Anti-Nuclear Antibodies (ANA) ELISA Kit (Cat #5200, Alpha Diagnostic International, Inc. San Antonio, Tex.) according to the manufacturer's instructions. This kit detects total ANA against ds-DNA, ss-DNA, histones, ribonucleoproteins (RNPs), SS-A, SS-B, SM antigens, Jo-1, and Scl-70. The results demonstrated that GTPs significantly (two tailed t-test, P<0.05) lowered the serum autoantibodies in GTPs-treated mice, by approximately 20% (FIG. 3).

Example 2

An animal study was conducted to examine whether EGCG fed prior to development of exocrinopathy is protective against salivary gland lymphocyte infiltration and gland abnormalities. Since EGCG is the most abundant green tea polyphenol, and widely used in scientific studies, this compound was selected for this feasibility study using 0.2% EGCG in drinking water (Gillespie K, et al. 2008).

Lymphocytic Infiltration in the Submandibular Glands.

Figure 4:
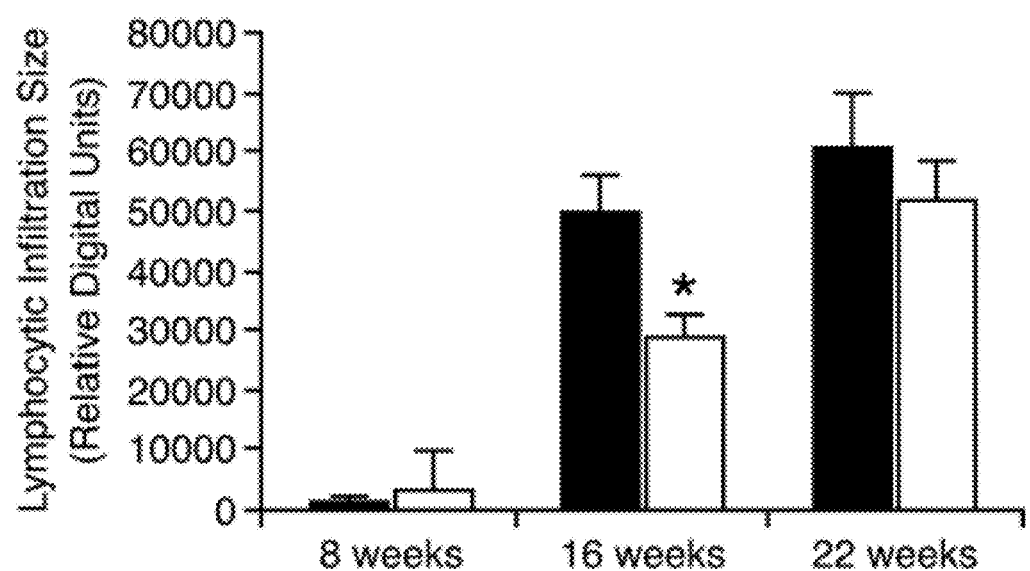
FIG. 4 shows average focal areas of submandibular gland lymphocyte infiltration in NOD/Lt mice at different age. Animals were fed either with EGCG/water or water only. At the age of 8 (n=36), 16 (n=36) and 22 weeks (n=27), submandibular glands were dissected, processed and stained by H&E. Three randomly selected areas of lymphocytic infiltrates were measured in each gland as relative density units generated by BIOQUANT NOVA PRIME 6.75 software, representing area sizes. Error bars are standard error of means (SEM). Results were analyzed by the two-tailed t-test analysis. *At 16 weeks of age, the average lymphocytic infiltrated area in EGCG-fed animals is significantly lower that in water-fed animals (p=0.026).

When the two treatment groups were compared at 16 weeks of age, the average area of lymphocytic infiltration in the EGCG-fed group was significantly lower (p=0.026). By the age of 22 weeks, when diabetes manifests in this animal model, there was no significant difference. That is, EGCG delayed (but did not prevent) the increase in lymphocytic infiltration of the NOD/Lt mouse submandibular glands (FIG. 4).

Apoptotic Activity in the Salivary Glands.

Figure 5:
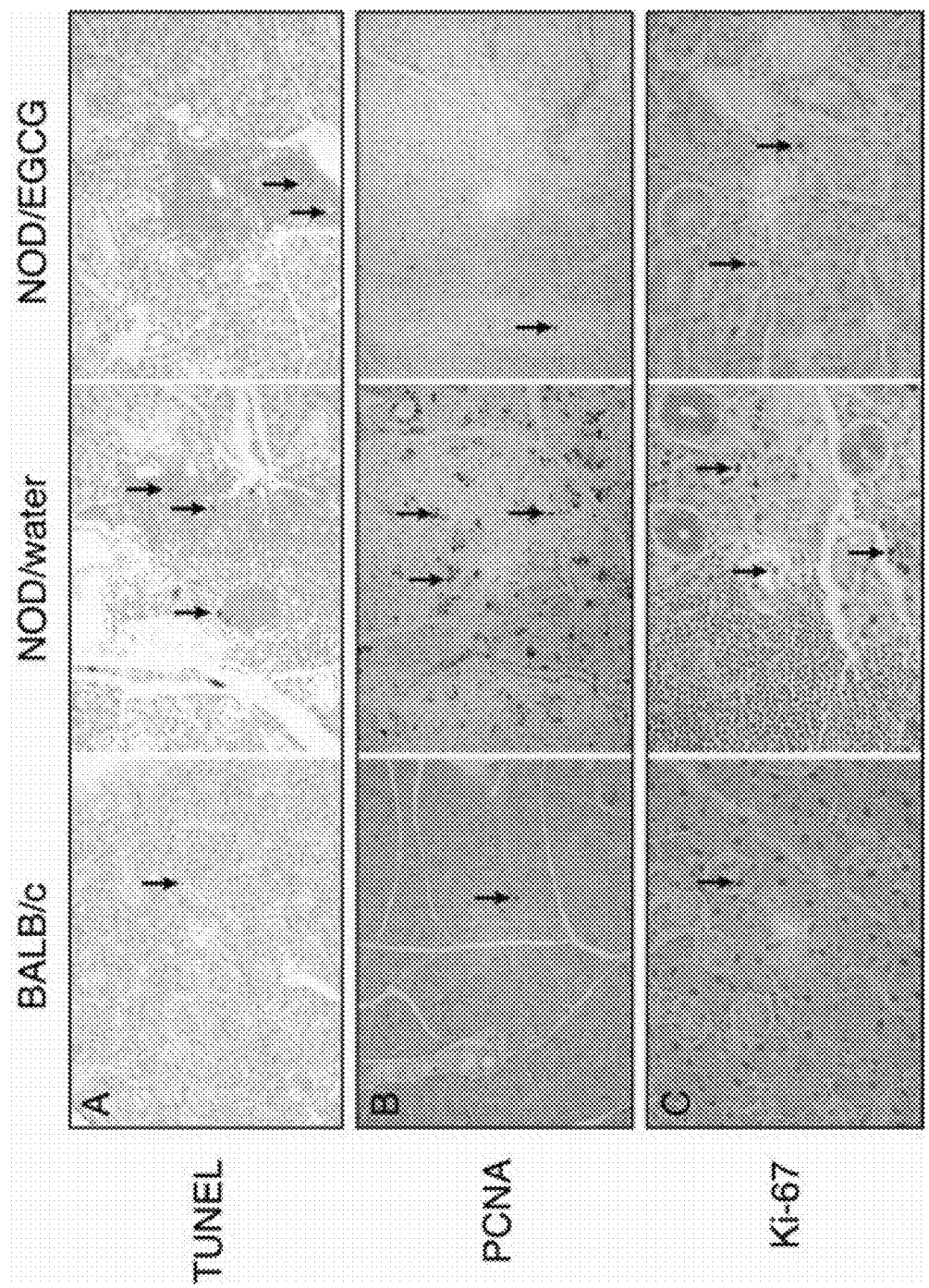
FIG. 5A shows representative TUNEL staining of submandibular glands from BALB/c, water-fed, and EGCG-fed NOD/Lt mice at 22 weeks of age (magnification 10×). Submandibular salivary gland samples from BALB/c (left), water-fed (middle), and EGCG-fed (right) NOD/Lt mice were stained with ApopTag Plus Peroxidase in situ apoptosis detection method according to the manufacturer's instructions. Arrows point to the nuclear staining of TUNEL-positive cells.
FIG. 5B shows representative PCNA immunostaining of submandibular glands from BALB/c, water-fed, and EGCG-fed NOD/Lt mice at 22 weeks of age (magnification 10×). Submandibular salivary gland samples from BALB/c (left), water-fed (middle), and EGCG-fed (right) NOD/Lt mice were immunostained with the anti-PCNA antibody. Arrows point to the nuclear staining of PCNA-positive cells.
FIG. 5C shows representative Ki-67 immunostaining of submandibular glands of BALB/c, water-fed, and EGCG-fed NOD/Lt mice at 22 weeks of age (magnification 40×). Submandibular salivary gland samples from BALB/c (left), water-fed (middle), and EGCG-fed (right) NOD/Lt mice were immunostained with the anti-Ki-67 antibody. Arrows point to the nuclear staining of Ki-67-positive cells.
Figure 6:
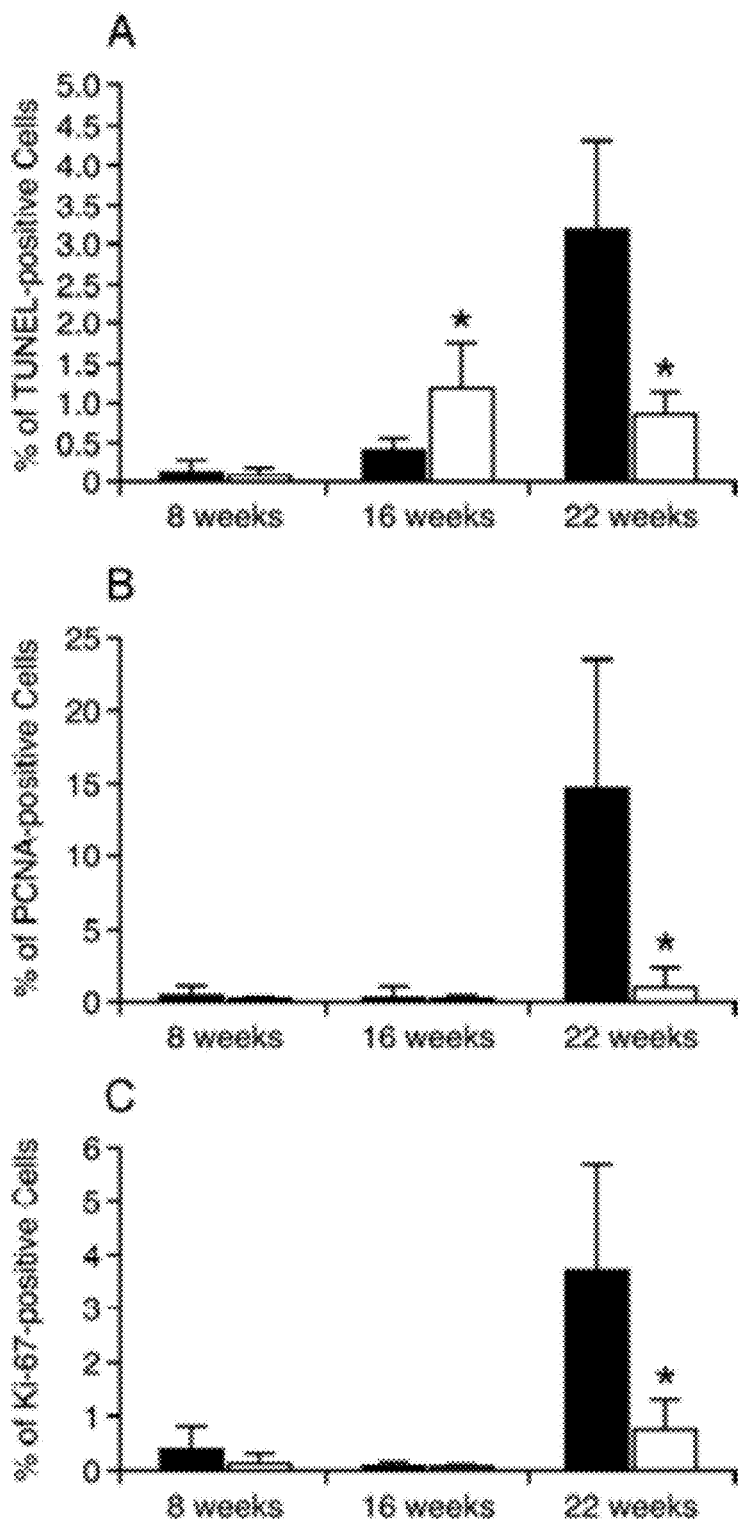
FIG. 6A shows percentage of TUNEL-positive cells in the submandibular gland epithelium of water-fed and EGCG-fed NOD/Lt mice at 8, 16, and 22 weeks of age. Solid bars represent the average percentage of TUNEL-positive cells in the submandibular gland of water-fed NOD/Lt mice. Open bars represent the average of TUNEL-positive cells in the submandibular gland of EGCG-fed NOD/Lt mice.
FIG. 6B shows percentage of PCNA-positive cells in the submandibular gland epithelium of water-fed and EGCG-fed NOD/Lt mice at 8, 16, and 22 weeks of age. Solid bars represent the average percentage of PCNA-positive cells in the submandibular gland of water-fed NOD/Lt mice. Open bars represent the average of PCNA-positive cells in the submandibular gland of EGCG-fed NOD/Lt mice.
FIG. 6C shows percentage of Ki-67-positive cells in the submandibular gland epithelium of water-fed and EGCG-fed NOD/Lt mice at 8, 16, and 22 weeks of age. Solid bars represent the average of Ki-67-positive cells in the submandibular gland of water-fed NOD/Lt mice. Open bars represent the average of Ki-67-positive cells in the submandibular gland of EGCGfed NOD/Lt mice. *Statistical difference was found between the two treatment groups. y-error bars represent SD.

The apoptotic activity was determined by TUNEL staining of the salivary glands (FIG. 5A) and quantification (FIG. 6A). EGCG did not affect the modest levels of apoptosis in the glandular epithelium, but did affect apoptosis in the infiltrates, initially raising levels, but blocking the considerable increase seen at 22 weeks in water-fed mice (FIG. 6A). Although it was not determined which cells were undergoing apoptosis, there was no significant apoptotic activity in the majority of secretory cells (Gillespie K, et al. 2008).

PCNA Expression in the Submandibular Glands.

Figure 7:
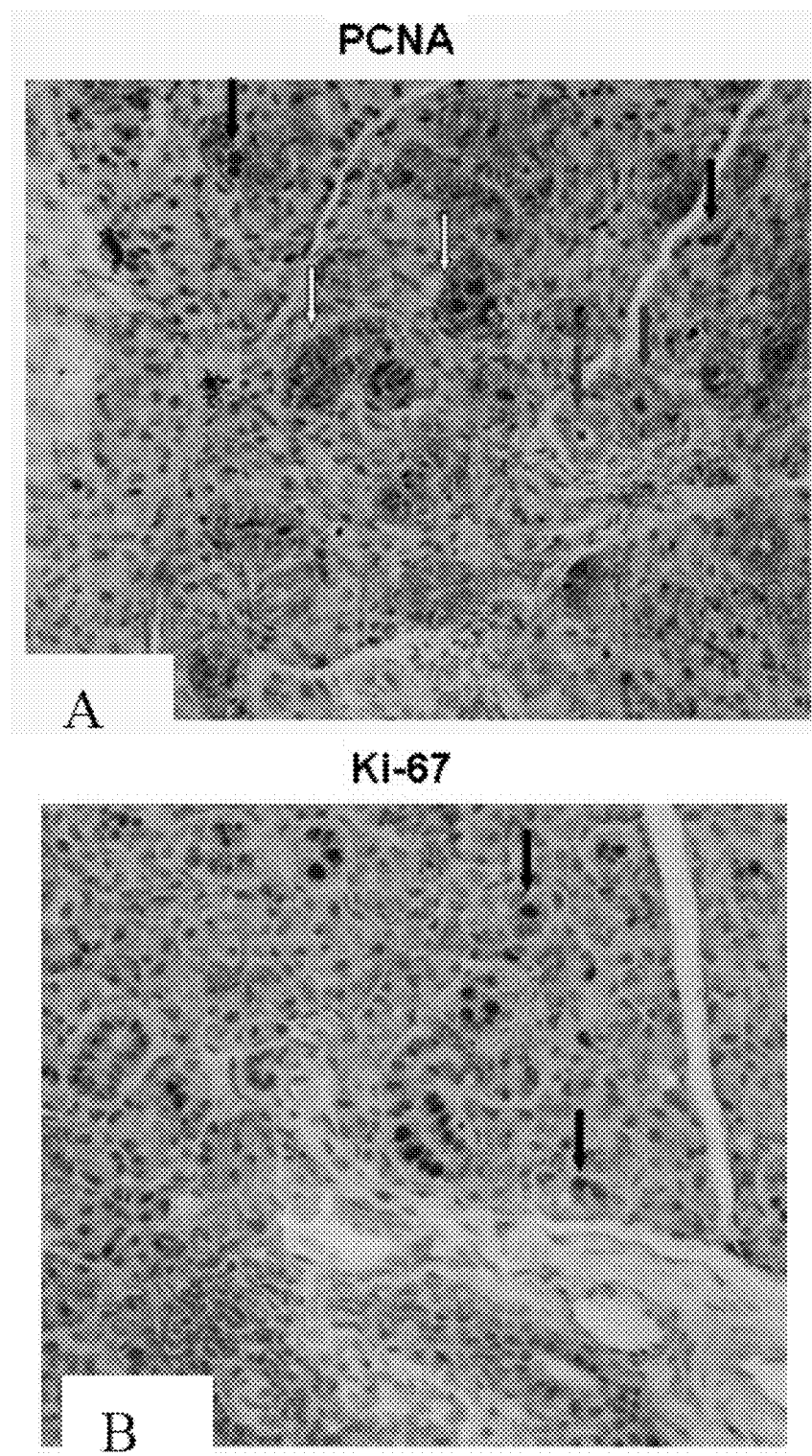
FIGS. 7A-7B show PCNA and Ki-67 expression in glandular epithelium of 22 week old water-fed animals (magnification 40×).
Figure 8A:
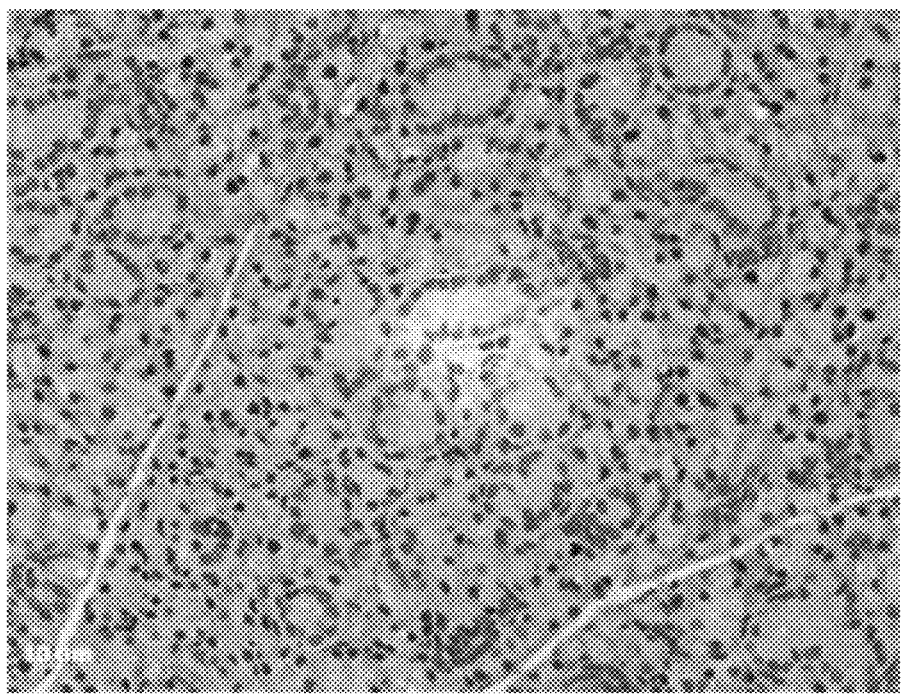
FIGS. 8A-8C, 8D-8F show representative immunostaining of peroxiredoxin 6 (FIGS. 8A-C) and catalase (FIGS. 8D-F) expression in glandular epithelium of 22 week old water-fed (FIGS. 8A, 8D) and EGCG-treated NOD mice (FIGS. 8B, 8E) (magnification 200×).
Figure 8B:
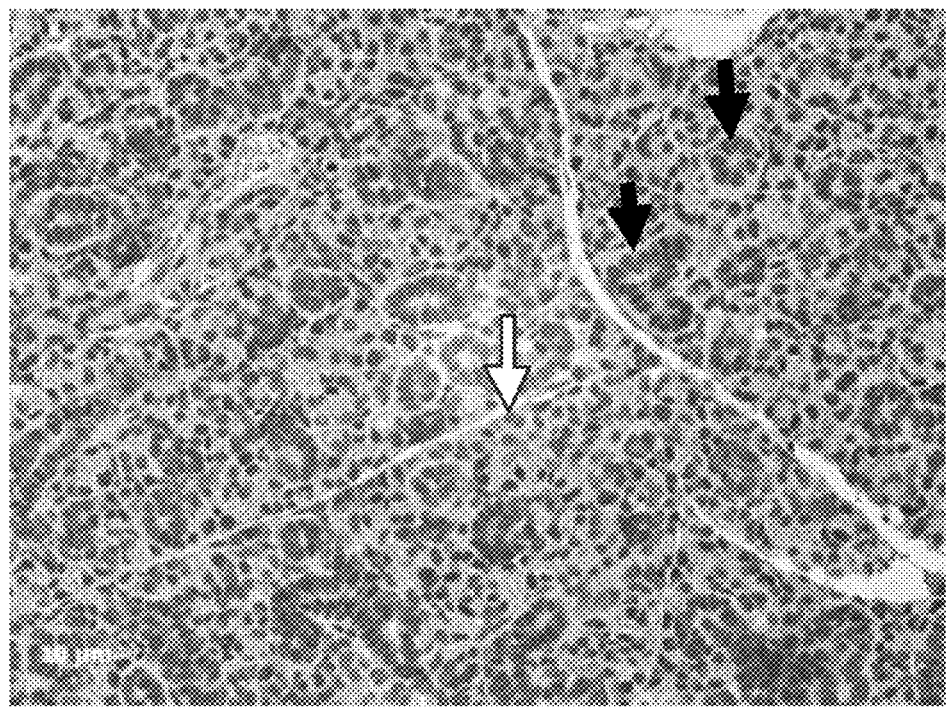
Figure 8D:
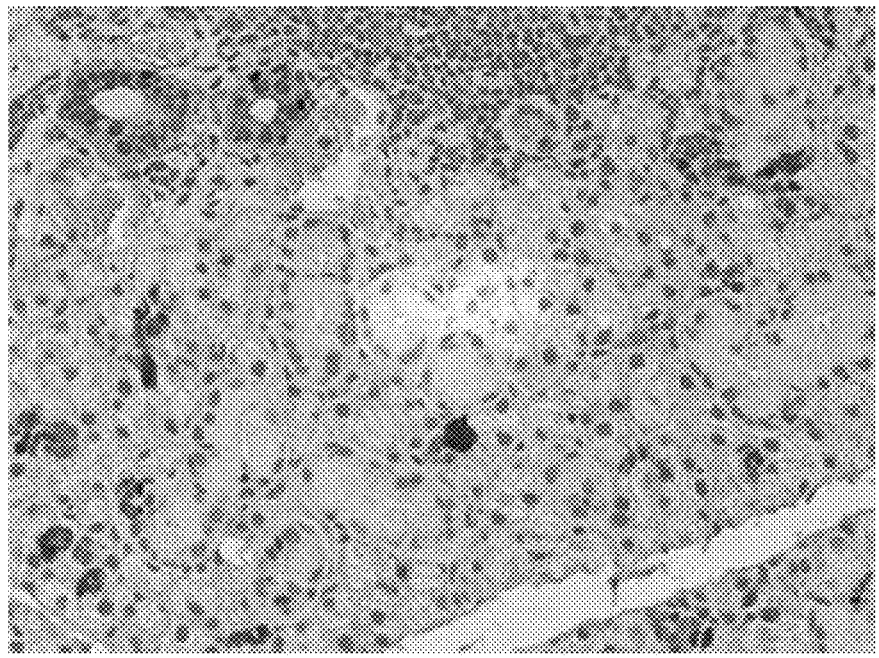
Figure 8E:
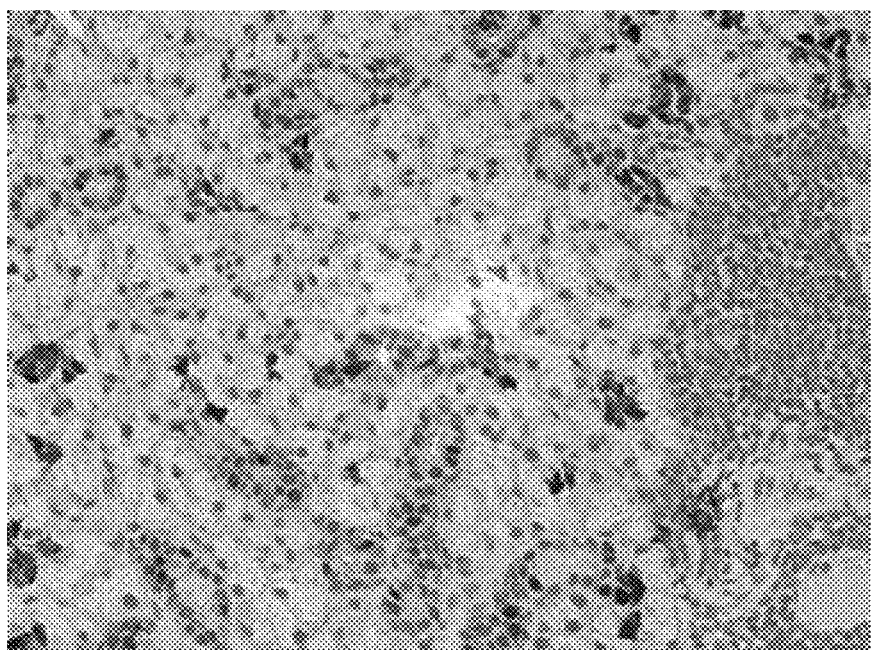
Figure 8C:
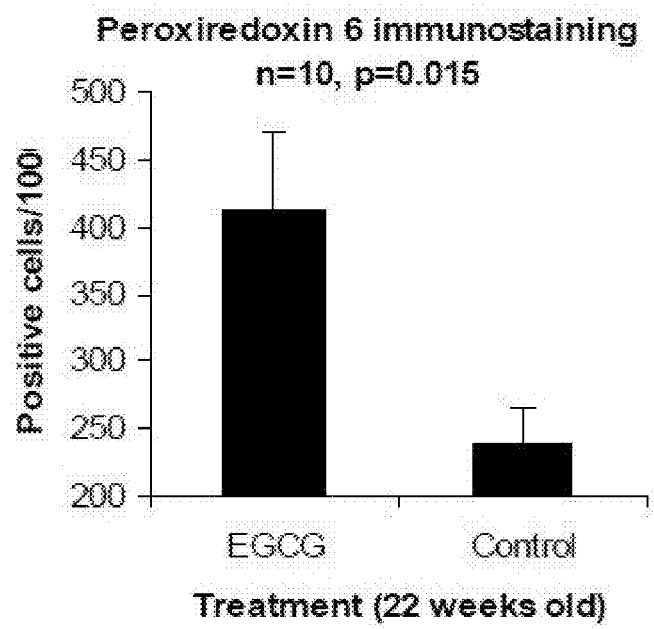
Figure 8F:
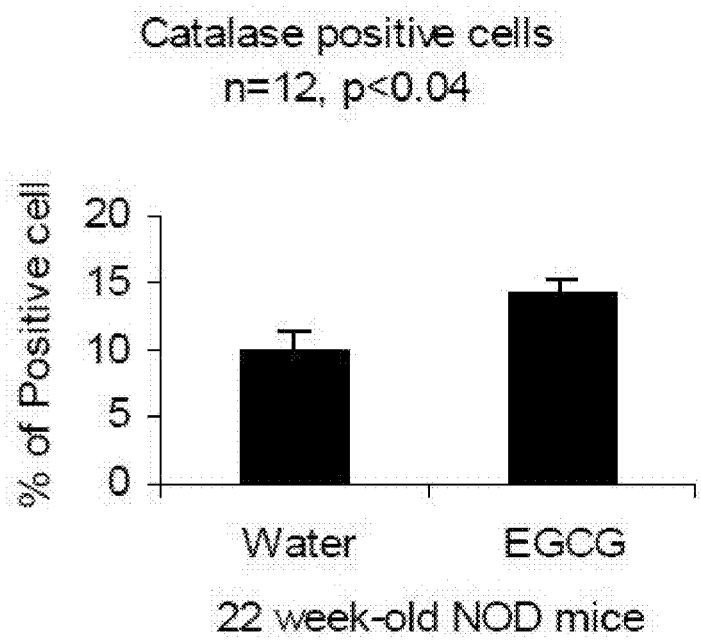
Figure 9A:
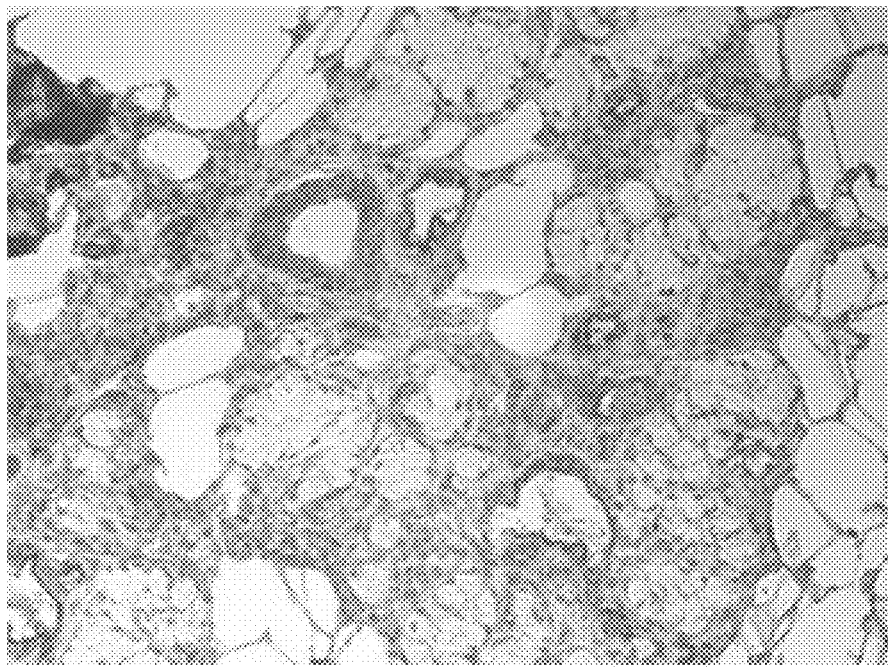
FIGS. 9A-C show representative immunostaining of PCNA (FIG. 9A), Ki-67 (FIG. 9B), and TUNEL (FIG. 9C) in human minor salivary glands from patients with Sjogren's syndrome (SS).
Figure 9B:
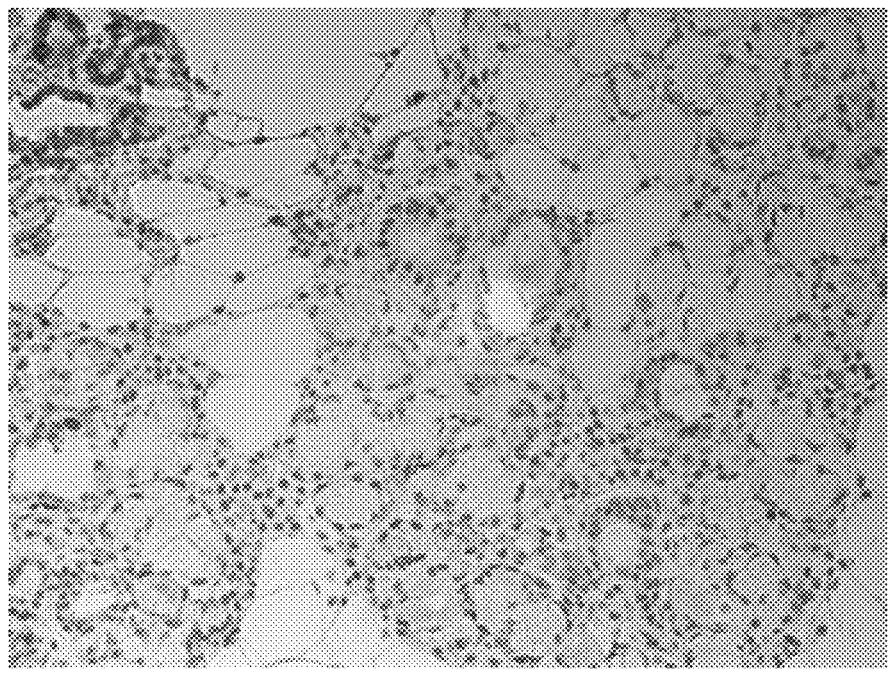
Figure 9C:
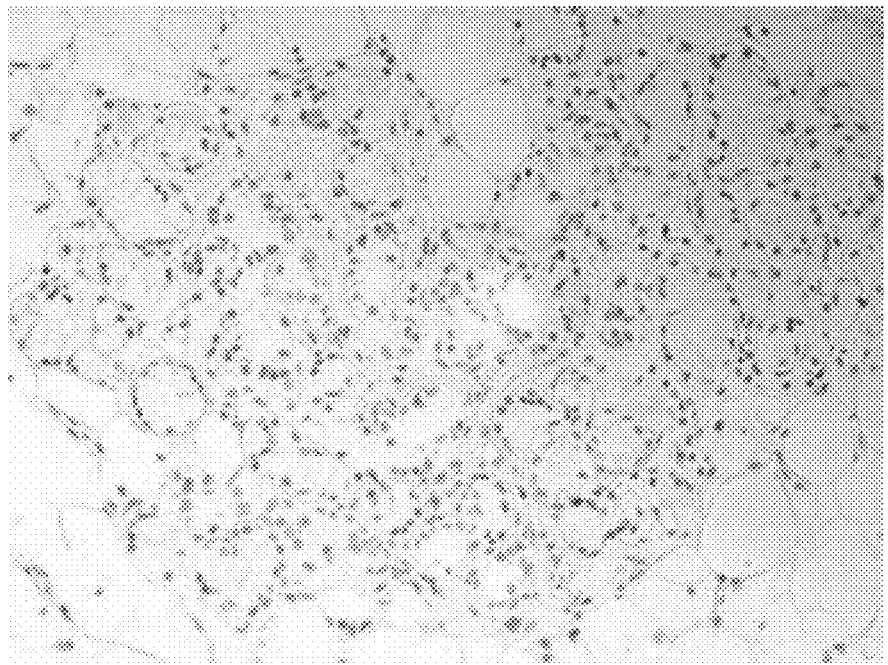
Figure 9D:
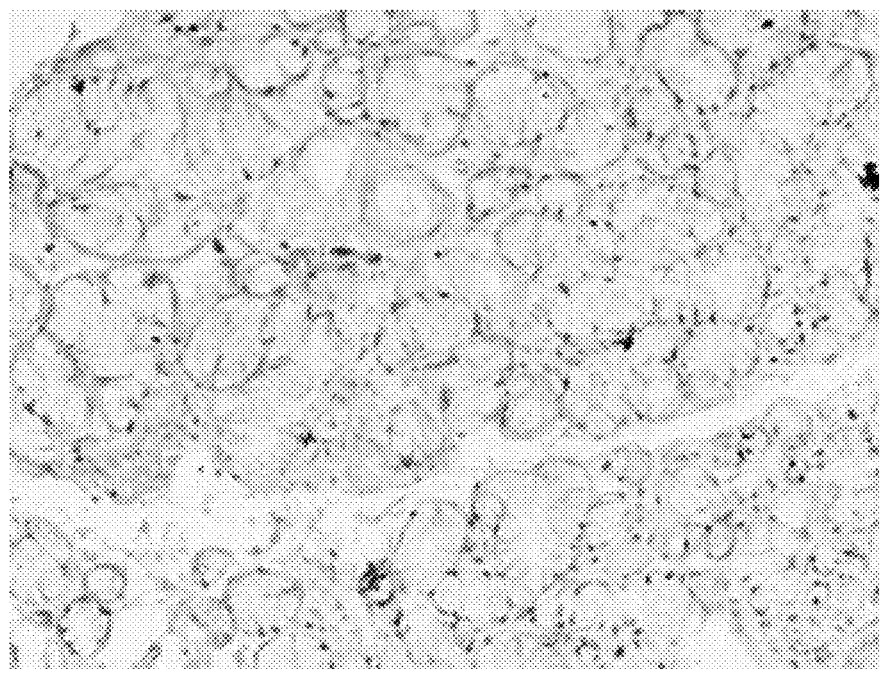
FIGS. 9D-F show representative immunostaining of PCNA (FIG. 9D), Ki-67 (FIG. 9E), and TUNEL (FIG. 9F) in control samples from normal individuals. Human minor salivary glands from SS patients show significantly elevated PCNA and Ki-67 expression in comparison to normal control, but low apoptotic activity in both SS patients and control samples.
Figure 9E:
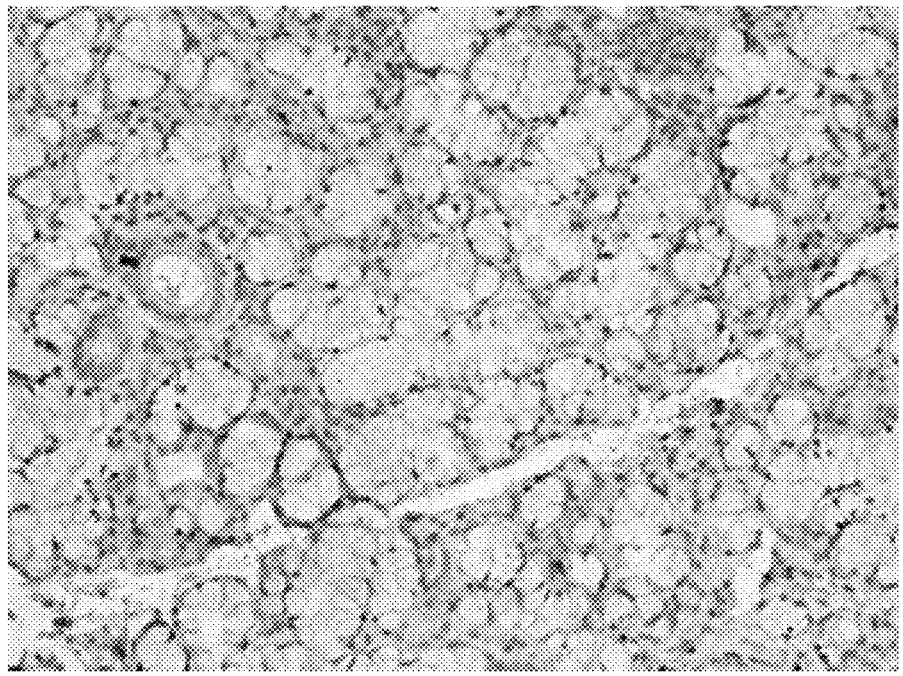
Figure 9F:
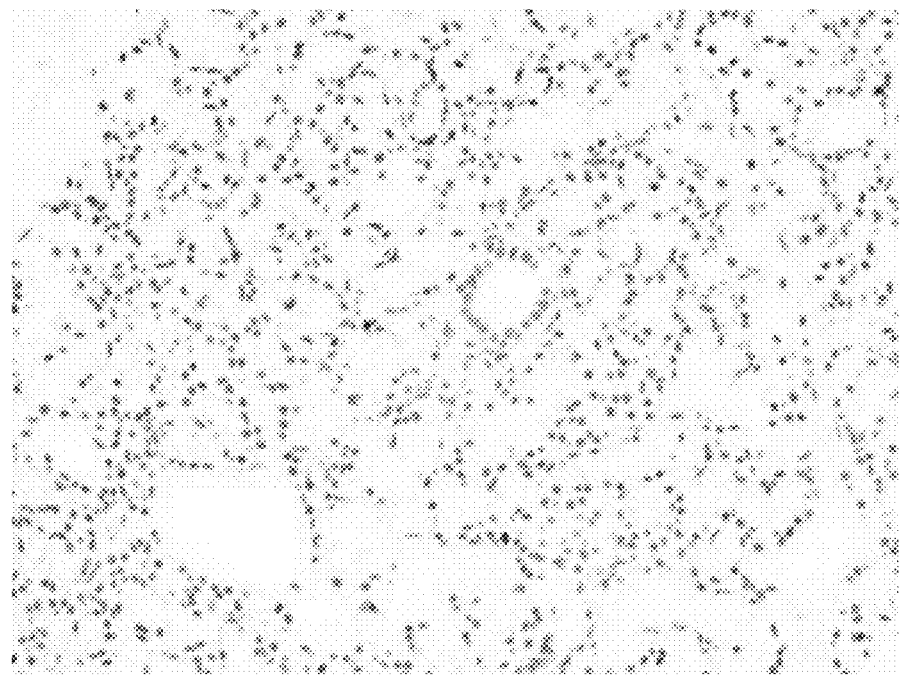

In water-fed NOD/Lt mice, there was a dramatic rise in PCNA-positive cells between 16 and 22 weeks of age (FIGS. 5B, 6B). EGCG considerably reduces the rise of PCNA between 16 and 22 weeks of age, and maintains levels comparable to normal control mice (FIGS. 5B, 6B). The vast majority of the PCNA-positive cells were localized to the ductal epithelial cells (FIG. 7A). Of these positive cells, most show cytoplasmic staining, but a significant minority show nuclear staining. Some ducts also showed PCNA immunostaining in the lumen (FIG. 7A).

Ki-67 Expression in the Submandibular Glands.

In NOD/Lt mice, Ki-67 levels behaved similarly to PCNA levels and were affected by EGCG in the same pattern (FIGS. 5C, 6C). The proportion of Ki-67-positive cells at 22 weeks of age in the water-fed group was almost a fourth of that of the PCNA-positive cells (3.71% vs. 14.64%). This was due to the fact that in the vast majority of the Ki-67-positive cells, the Ki-67 signal was localized to the nuclei of ductal epithelial cells (FIG. 7B), while PCNA, in addition to nuclear localization, was also found in the cytoplasm of a substantial proportion of ductal cells, and it was even secreted into the lumen (FIG. 7A).

Example 3

EGCG elevates the antioxidant capacity in NOD mice. Proteomic analysis demonstrated reduced levels of peroxiredoxin 6 in NOD mice fed with water only. Screening of other antioxidant enzymes found reduced levels of catalase.

Salivary gland and pancreas samples were obtained at 22 weeks of age from NOD mice fed water or EGCG-water (12 animals per group), and from control BALB/c mice. The antioxidant capacity represented by protein levels of peroxiredoxin 6, superoxide dismutase 1 (SOD1), catalase, and glutathione peroxidase was measured by immunohistochemstry.

As shown in FIG. 8, expression of peroxiredoxin 6 and catalase in the submandibular salivary glands of EGCG-fed NOD/Lt mice was significantly higher than levels in the water only fed mice, consistent with the protective effects of EGCG (n=12, p<0.04). In the pancreas, peroxiredoxin 6 and SOD1 were depleted in water only NOD mice, but were normalized to BALB/c levels by EGCG (n=12, P<0.0001).

Thus, the antioxidant effects of EGCG are associated with an induction of certain antioxidant enzymes, thereby increasing the antioxidant capacity in targets tissues affected by the autoimmune reaction in NOD mice.

Example 4

Labial minor salivary gland biopsies from xerostomia patients (mostly Sjogren's syndrome patients) were collected. The antioxidant, proliferation, and apoptosis indexes were established for each patient using immunohistochemistry methods. Patient data were analyzed in comparison to results previously obtained from our animal model for SS.

Hyperproliferation in glandular epithelial cells was found in xerostomia patients, regardless of SS status. Apoptotic activity was not significant in the salivary glands. Human SS minor salivary glands demonstrate hyper-proliferation but minimal apoptotic activity, similar to NOD mice. Immunohistochemistry demonstrated elevated PCNA and Ki-67 in both ductal and acinar cells, but few apoptotic cells (FIG. 9), consistent with results from NOD mice. Glands from normal volunteers show minimal immunostaining of PCNA and Ki-67 (FIG. 9).

Thus, reduced antioxidant capacity and hyperproliferation can serve as biomarkers and be targeted by green tea polyphenols as a novel therapeutic approach to xerostomia.

Example 5

Minor salivary gland biopsies from xerostomia patients (mostly Sjogren's syndrome patients) were collected. Patient diagnosis, pathological, serological data were analyzed in comparison to the antioxidant capacity represented by protein levels of peroxiredoxin 6, superoxide dismutase, catalase, and glutathione peroxidase, measured by immunohistochemistry. Antioxidant, proliferation, and apoptosis indexes were established for each patient.

Figure 10A:
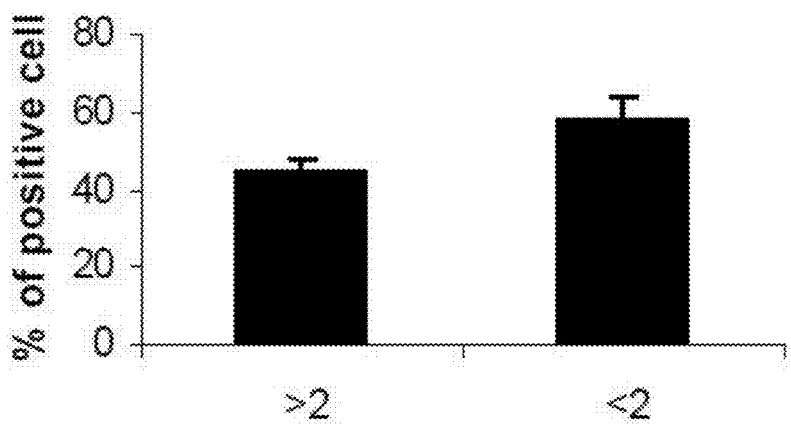
FIGS. 10A-10B show statistical analysis of minor salivary glands immunohistochemistry data from 13 patients categorized by focal scores. Patients with focal score >2 showed significantly reduced peroxiredoxin 6 (FIG. 10A) and glutathione peroxidase 1 (FIG. 10B) levels (p<0.05).
Figure 10B:
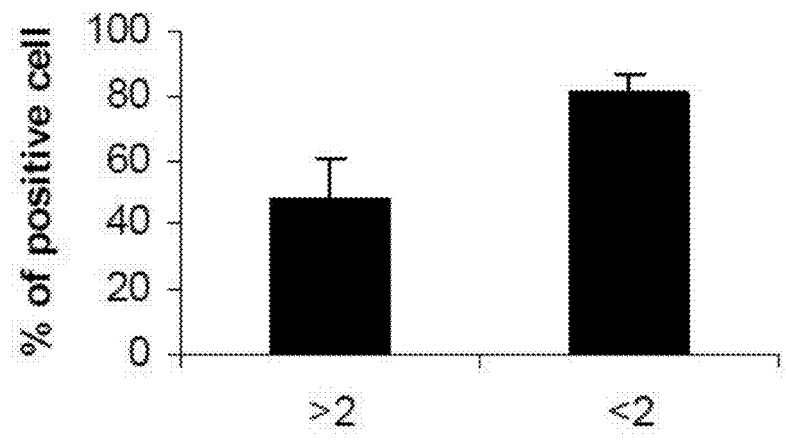

As shown in FIG. 10, SS patient minor salivary glands also demonstrate decreased antioxidant enzyme levels. Among a group of 13 patients, expression of two key antioxidant enzymes, peroxiredoxin 6 and glutathione peroxidase 1, was significantly reduced in patients with a focal score >2, in comparison to patients with a focal score <2 (n=13, p<0.05), which is consistent with the disclosed animal data (FIG. 8). All xerostomia patients exhibited an increased proliferation index, and minimal levels of apoptosis.

Thus, xerostomia induced by Sjogren's syndrome is associated with altered antioxidant capacity in the salivary gland, and elevated proliferation, but not apoptotic activity. These characteristics can therefore be used as targets for novel therapeutics.

Example 6

Figure 11:
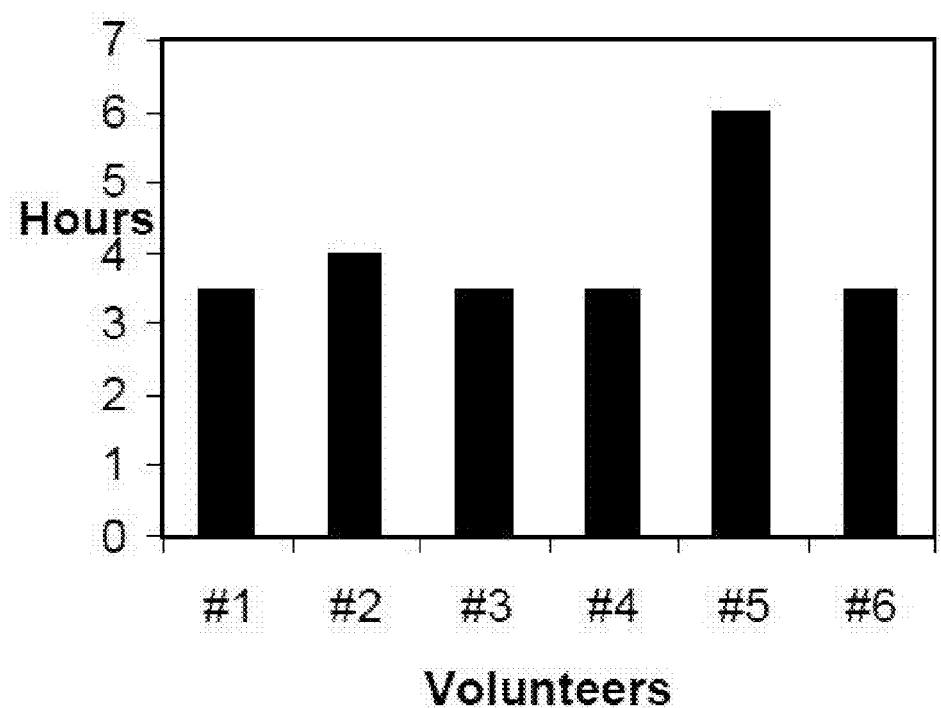
FIG. 11 shows duration of elevated salivation in healthy volunteers. Six volunteers used the disclosed formula containing green tea extract and *jaborandi* extract at time 0. Each volunteer reported the duration of elevated salivation blindly and separately.

Un-stimulated salivation lasted 3-4 hours/dose in healthy volunteers (FIG. 11). A total of 6 volunteers were given a mint containing sorbitol (~800 mg), green tea powder (~120 mg), calcium stearate, acesulfame potassium, aspartame, natural flavors, and sodium dioxide. The green tea mint was placed in the oral cavity with 10 mg *jaborandi* leaf extract (B&K Technology Group (China) Co., Ltd.). Other volunteers took the mint without the *jaborandi* extract. Each volunteer was then asked to record the duration of noticeable elevated salivation, without communicating to each other. At the end of the test, 4 reported a 3.5 h duration and one reported a 6 h duration of sustained hyper-salivation. The average duration of hyper-salivation was 4 hours, with 1.12 hour of standard deviation (FIG. 11).

Therefore, affected glands display not only lymphocytic infiltration (as seen in humans), but also hyperproliferation of epithelial cells (represented by elevated PCNA and Ki-67), modest apoptosis and a decrease in antioxidant capacity (i.e., lower peroxiredoxin 6 and catalase levels). GTP/EGCG reduce inflammation, apoptosis, and elevate peroxiredoxin 6 and catalase. As disclosed herein, there is hyperproliferation, modest apoptosis and a decrease in antioxidant capacity (including peroxiredoxin 6) in human SS salivary glands in addition to inflammation. This validates the mouse model.

Example 7

Disclosed is a clinical study that uses an open-label design involving 30 patients with subjective complaints of dry mouth (xerostomia), including SS-mediated salivary gland hypofunction. The number was chosen on a power analysis using estimates of the coefficient of variation for stimulated whole salivary flow rate (SWSFR, 0.63) and unstimulated whole salivary flow rate (UWSFR, 1.10) based on published data. A sample size of n=30 subjects can yield 80% power for detecting an improvement of at least 37% in SWSFR and 65% in UWSFR when comparing baseline with either Week 4 or Week 8 using a Bonferroni-adjusted significance level of 0.025. The coefficient of variation for quality of life (QOL) is estimated to be 0.58, and a sample size of n=30 subjects an yield 80% power for detecting at least a 34% improvement in QOL using a Bonferroni-adjusted significance level of 0.025. The power for the Tukey-Kramer analysis can be even greater since the Bonferroni is a conservative method for performing pairwise comparisons.

Study Population and Recruitment.

Eligibility criteria for enrollment of subjects include 1) a complaint of dry mouth as assessed by a response of 30 mm or greater on a Dry Mouth Visual Analog Scale (VAS), 2) primary or secondary Sjogren's syndrome, 3) an unstimulated whole salivary flow rate of <0.2 mL/min, 4) over the age of 18, 5) taking less than three drugs associated with causing xerostomia or salivary gland hypofunction, 6) willing to use natural novel topical dry mouth products, 7) willing to return for all study-associated visits, and 8) able to read, understand, and sign the informed consent.

Exclusion criteria include 1) past radiation to the head and neck region, 2) inability to read and understand the consent form, 3) using more than three drugs associated with xerostomia or salivary gland hypofunction, 4) requirement of dento-alveolar surgery or extensive dental treatment during the course of the study, 5) hospitalization requirement for any medical problem during the course of the study, 6) inability to take green tea leaf extract and/or *pilocarpus jaborandi* leaf extract, 7) uncontrolled medical conditions that require changes in medication during the course of the study, and 8) regular consumption of green tea and/or components of *pilocarpus jaborandi*.

Potential candidates are identified from a pool of previously diagnosed subjects and new subjects referred to the Clinical Center for Oral Medicine. Candidates are given a simple explanation of the study and questioned as to their willingness to participate. Those subjects expressing a desire to volunteer are formally screened for eligibility. No monetary participation incentive is offered. However, subjects are reimbursed for travel costs and parking. Appropriate measures are taken to protect the privacy of study volunteers per established MCG policies.

Study Design.

Volunteers receive the test article daily for 4 weeks. Each unit of 2 g contains a formula mix of green tea extract (50 mg green tea catechins), in a proprietary formula containing other natural ingredients. This formula is finalized by the manufacturer.

Subjects are evaluated once prior to initiation of therapy (between weeks −4 and −1), at the initiation of therapy (week 0), completion of therapy (week 4) and 4 weeks after completion of therapy (week 8) according to Table 2.

TABLE 2

Patient evaluation methods to be used. SCR, initial screening.

| | SCR | Week 0 | Week 4 | Week 8 |
|---|---|---|---|---|
| Informed Consent | X | | | |
| Eligibility | X | | | |
| Oral Examination | X | X | X | X |
| VAS and QOL Assessment | X | X | X | X |
| Sialometry | | X | X | X |
| Minor Salivary Gland Biopsy | X | | X | |
| Serology | X | | X | X |

Laboratory Evaluations.

Hematology, serum chemistry, antinuclear antibody (ANA), anti-Ro (SSA) and anti-La (SSB) and rheumatoid factor (RF) evaluations are ordered if not already done.

Clinico-Pathological Analysis.

Histopathological evaluation of the inflammatory cell infiltrates in minor salivary glands is an effective diagnostic indicator for SS. This is performed by an oral pathologist experienced in SS salivary pathology.

Immunohistochemistry Analysis of Proliferation, Apoptosis and Preoxyredoxin 6.

Minor salivary gland sections is immuno-stained with antibodies specific for human PCNA and Ki-67 to establish a cell proliferation index, or TUNEL stained for an apoptosis index. Other sections are immuno-stained with an antibody specific for peroxyredoxin 6. The images are captured as digital files and quantified as described previously (Gillespie K, et al. 2008).

Visual Analog Scale (VAS)—Xerostomia.

A 100-mm visual analog scale (VAS) is used to record the responses to each of six questions addressing the patient's degree of oral dryness. The scale is set up with negative responses on the left and positive responses on the right. The patients mark their responses on the scale in relation to these extremes and the distance in millimeters from the leftmost portion of the scale is measured. In each analysis, the score at baseline is subtracted from the later scores to assess change. Overall improvement after therapy is assessed on the basis of three categories of responses (better, worse, no change).

Quality of Life Assessment (QOL).

Patients answer a survey administered by either the clinical research coordinator or a co-investigator using a previously validated questionnaire determining QOL and an assessment of oral comfort using a 100-mm VAS to assess 6 clinical questions. The scale is set up with negative responses on the left and positive responses on the right. The subjects mark their responses on this scale, and baseline scores are subtracted as described above for VAS, to assess change in oral comfort. Patients are not allowed to consult with one another while completing their surveys.

There is a large variation in salivary function in a normal population. Even among patients with complaints of dry mouth and diminished salivary function, there is great variability in measured salivary flow. For this reason, it is essential to establish baseline salivary flow data for each subject in a study. Additionally, an individual's flow will vary markedly during the day, due to responses to exogenous stimuli and circadian rhythms. It is therefore critical to control collection techniques and external variables as much as possible. All saliva collections are done within a specified time period of the day (usually between 8 and 11 am). When unstimulated secretions are to be collected, subjects fast for a minimum of 90 minutes prior to collection. During this period, any oral stimulants should be avoided (e.g., no smoking, tooth brushing, drinking, chewing gum, etc.). Collections are done in a climate-controlled facility with a comfortable examination chair and the subject sitting upright. The subject is seated at least 15 minutes before the collection begins. The subject can answer questions or complete a questionnaire during this time, but an oral exam is not be done prior to saliva collection. Subjects are instructed not to attempt to increase or control salivation actively, but simply to relax. If these details are followed, one can expect less than 10% variability with repeat saliva collections on an individual over time.

Saliva Collection Method.

To avoid diurnal variation in salivary flow, all collections are performed at the same time of day. Patients are asked to refrain from eating, drinking or smoking for at least 90 minutes prior to saliva collection. Saliva collection is a noninvasive technique and no hazards have been associated with the described techniques. These means of salivary collection are well-accepted procedures for salivary gland diagnosis. They have been selected to minimize patient discomfort by avoiding cannulation of the ducts or extensive mucosal contact. The measurements described below should require no longer than 30 minutes to perform from start to finish. Salivary flow rates are determined gravimetrically in ml per min assuming that saliva specific gravity is 1 (i.e., 1 gram equals 1 ml saliva).

Un-Stimulated Whole Saliva Flow Rate (UWSFR).

The spitting method is utilized. The patient is asked to allow saliva to accumulate in the floor of their mouth and the patient will expectorate into a pre-weighted test tube every 60 seconds for five minutes.

Stimulated Whole Saliva Flow Rate (SWSFR).

The patient is asked to chew a standardized size of pre-weighted paraffin wax at a controlled rate. The patient will be asked to allow the saliva to accumulate in their mouth and expectorate into a pre-weighted test tube every 60 seconds for 5 minutes. After 5 minutes of stimulation the patient will expectorate the paraffin into the test tube.

Statistics.

In brief, results for all outcome variables (saliva flow rate, quality of life assessment, etc.) are analyzed using a single-group repeated measures ANOVA with "time point" as the within factor. Random effects regression models (RRMs) are used, if necessary, to adjust for the effects of any significant subject-specific variables (age, cause of xerostomia, etc.). The Tukey-Kramer method for repeated measures is used to perform all pairwise comparisons among the time points. The use of RRMs enables incorporation of all available data into the analysis, even if there are missing observations at some time points. If the data appear to violate the normality assumption, rank-based repeated measures analysis is used. A significance level of $\alpha=0.05$ is used for all tests. All analyses is performed using PROC MIXED in SAS.

Data Management.

Data collection is via paper forms which are then scanned into the patient's secure electronic health record stored in an Axium data management system. There will be limited access to these records. Appropriate measures are taken to protect the privacy of study volunteers and maintain confidentiality of study data. Hardcopy records are maintained and secured in clinical files. In cases where the volunteer might benefit medically from information obtained in this study, that information is shared with the subjects medical provider.

The disclosed study determines that the disclosed formulation offers a strategy with immediate clinical application for the amelioration of xerostomia, and provides improvement in salivary gland pathology in SS.

REFERENCES

Baudouin C, Pisella P J, Brignole F. Current treatments of xerophthalmia in Sjögren's syndrome]. Rev Med. Interne. 2004, 25:376-82.

Cassolato S F, Turnbull R S. Xerostomia: clinical aspects and treatment. Gerodontology. 2003, 20:64-77.

Fox R I. Sjögren's syndrome. Controversies and progress. Clin Lab Med. 1997 September; 17(3):431-44.

Fox R I. Sjogren's syndrome: evolving therapies. Expert Opin Investig Drugs. 2003, 12:247-54.

Gillespie K, Kodani I, Dickinson D P, et al. Effects of oral consumption of the green tea polyphenol EGCG in a murine model for human Sjogren's syndrome, an autoimmune disease. 2008. Life Sciences, 83:581-588.

Hsu S and Dickinson D. Green Tea: A New Approach to Managing Oral manifestations of Sjogren's Syndrome and Skin Manifestations of Lupus Journal of Biochemistry and Molecular Biology. 2006, 39: 229-39.

Hsu S, Dickinson D P, Qin H, et al. Green tea polyphenols reduce autoimmune symptoms in a murine model for human Sjogren's syndrome and protect human salivary acinar cells from TNF-alpha-induced cytotoxicity. 2007. Autoimmunity. 40(2):138-47.

Porter S R, Scully C, Hegarty A M. An update of the etiology and management of xerostomia. Oral Surg Oral Med Oral Pathol Oral Radiol Endod. 2004, 97:28-46.

Sreebny L M, Valdini A. Xerostomia. A neglected symptom. Arch Intern Med. 1987, 147:1333-7.

What is claimed is:

1. A method of treating xerostomia comprising administering to a subject in need thereof an effective amount of an oral care composition comprising (1) 10 mg/unit to 100 mg/unit of green tea extract comprising at least one green tea polyphenol (GTP) or a pharmaceutically acceptable salt or ester thereof and (2) 5 mg/unit to 50 mg/unit of *Jaborandi* extract.

2. The method of claim 1, wherein the subject has an autoimmune disease.

3. The method of claim 1, wherein the subject has Sjögren's syndrome.

4. The method of claim 1, wherein the subject has recently undergone radiation or chemotherapy.

5. The method of claim 1, wherein the subject has diabetes.

6. The method of claim 1, wherein the GTP has the following chemical structure or the pharmaceutically acceptable salt or ester thereof:

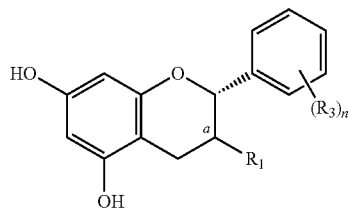

wherein $R_1$ is H, OH or gallic acid (GA);
$R_3$ is OH;
n is from 1 to 5; and
the stereochemistry at carbon a is substantially R or S.

7. The method of claim 1, wherein the GTP has the following chemical structure or the pharmaceutically acceptable salt or ester thereof:

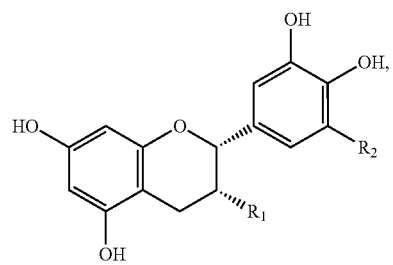

wherein $R_1$ is H, OH or gallic acid (GA), and
wherein $R_2$ is OH or H.

8. The method of claim 1, wherein the GTP is epigallocatechin-3-gallate (EGCG) or the pharmaceutically acceptable salt or ester thereof.

9. The method of claim 1, wherein the GTP has the following chemical structure or the pharmaceutically acceptable salt or ester thereof:

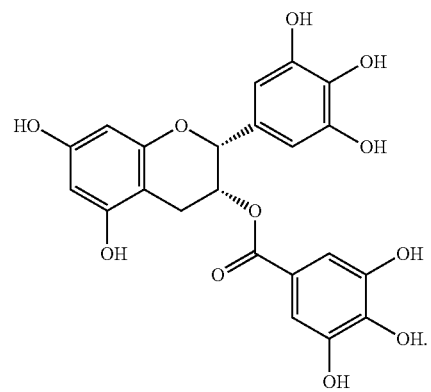 [SMILES: O=C(O[C@@H]1Cc2c(O)cc(O)cc2O[C@@H]1c1cc(O)c(O)c(O)c1)c1cc(O)c(O)c(O)c1]

10. The method of claim 1, wherein the GTP is epigallocatechin (EGC) or the pharmaceutically acceptable salt or ester thereof.

11. The method of claim 1, wherein the GTP has the following chemical structure or the pharmaceutically acceptable salt or ester thereof:

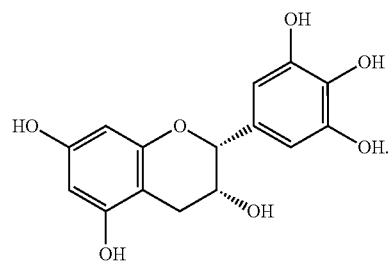 [SMILES: Oc1cc(O)c2c(c1)O[C@H](c1cc(O)c(O)c(O)c1)[C@H](O)C2]

12. The method of claim 1, wherein the GTP is epicatechin gallate (ECG) or the pharmaceutically acceptable salt or ester thereof.

13. The method of claim 1, wherein the GTP has the following chemical structure or the pharmaceutically acceptable salt or ester thereof:

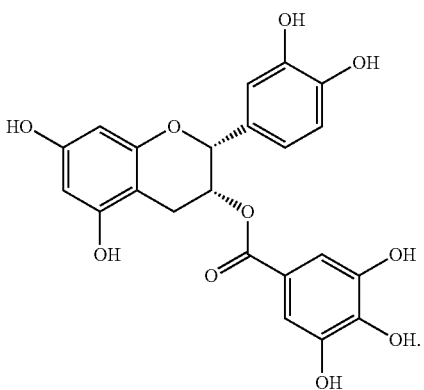 [SMILES: O=C(O[C@@H]1Cc2c(O)cc(O)cc2O[C@@H]1c1ccc(O)c(O)c1)c1cc(O)c(O)c(O)c1]

14. The method of claim 1, wherein the GTP is epicatechin (EC) or the pharmaceutically acceptable salt or ester thereof.

15. The method of claim 1, wherein the GTP has the following chemical structure or the pharmaceutically acceptable salt or ester thereof:

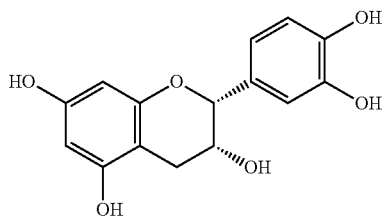 [SMILES: Oc1cc(O)c2c(c1)O[C@H](c1ccc(O)c(O)c1)[C@H](O)C2]

16. The method of claim 1, wherein the GTP is catechin (+C) or the pharmaceutically acceptable salt or ester thereof.

17. The method of claim 1, wherein the GTP has the following chemical structure or the pharmaceutically acceptable salt or ester thereof:

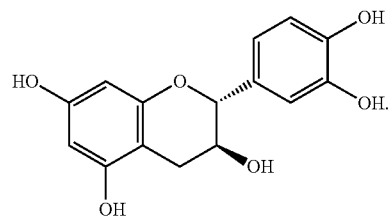 [SMILES: Oc1cc(O)c2c(c1)O[C@H](c1ccc(O)c(O)c1)[C@@H](O)C2]

18. The method of claim 1, wherein the *Jaborandi* extract comprises pilocarpine.

19. The method of claim 1, wherein the oral care composition comprises at least one taste stimulating component.

20. The method of claim 19, wherein the at least one taste stimulating component is citric acid, isocitric acid, malic acid, acetic acid, oxalic acid, malonic acid, succinic acid, glutaric acid, maleic acid, fumaric acid, aconitic acid, lactic acid, tartaric acid, pyruvic acid, ascorbic acid, aldonic acid, uronic acid, sodium glutamate, inosinic acid, or any combination thereof.

21. The method of claim 19, wherein the at least one taste stimulating component is citric acid.

22. The method of claim 1, wherein the oral care composition further comprises xylitol.

23. The method of claim 1, wherein the oral care composition is a dentifrice preparation.

24. The method of claim 1, wherein the oral care composition further comprises an orally acceptable carrier or excipient.

25. The method of claim 1, wherein the oral care composition comprises 10 mg/unit to 100 mg/unit of the one or more GTPs.

26. The method of claim 1, further comprising an orally acceptable carrier or excipient.

27. The method of claim 1, wherein the composition comprises 100 mg/unit green tea extract.

28. The method of claim 1, wherein the composition comprises 20 mg/unit of *Jaborandi* extract.

29. The method of claim 27, wherein the composition comprises 20 mg of *Jaborandi* extract.

* * * * *